(12) United States Patent
Kim et al.

(10) Patent No.: US 10,307,373 B2
(45) Date of Patent: Jun. 4, 2019

(54) DRUG DELIVERY FORMULATION FOR CONTROLLING OF INITIAL BURST AND MANUFACTURING METHOD THEREOF

(75) Inventors: Moon Suk Kim, Yongin-si (KR); Da Yeon Kim, Yangsan-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 459 days.

(21) Appl. No.: 13/022,734

(22) Filed: Feb. 8, 2011

(65) Prior Publication Data

US 2012/0177740 A1  Jul. 12, 2012

(30) Foreign Application Priority Data

Jan. 12, 2011  (KR) ........................ 10-2011-0003271

(51) Int. Cl.
| | |
|---|---|
| *A61K 9/10* | (2006.01) |
| *A61K 9/00* | (2006.01) |
| *A61K 9/16* | (2006.01) |
| *A61K 9/50* | (2006.01) |
| *A61K 47/34* | (2017.01) |
| *A61K 38/00* | (2006.01) |

(52) U.S. Cl.
CPC .............. *A61K 9/10* (2013.01); *A61K 9/0024* (2013.01); *A61K 9/1647* (2013.01); *A61K 9/1694* (2013.01); *A61K 9/5031* (2013.01); *A61K 9/5089* (2013.01); *A61K 47/34* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,543,158 A * | 8/1996 | Gref et al. ..................... | 424/501 |
| 6,120,787 A | 9/2000 | Gustafsson | |
| 2004/0175429 A1* | 9/2004 | Alavattam et al. ............ | 424/490 |
| 2005/0113299 A1* | 5/2005 | Mann ................... | A61K 38/164 |
| | | | 424/184.1 |

FOREIGN PATENT DOCUMENTS

KR  10-2004-0018407  3/2004

OTHER PUBLICATIONS

Wheatley, M. A., et al., Coated Alginate Microspheres: Factors Influencing the Controlled Delivery of Macromolecules, Journal of Applied Polymer Science, vol. 43 (1991), pp. 2123-2135.*
Yeo, Yoon, et al., Control of Encapsulation Efficiency and Initial Burst in Polymeric Microparticle Systems, Arch Pharm Res, vol. 27 (2004), pp. 1-12.*
Joung, Yoon Ki et al., Biomed. Mater. 2 (2007) pp. 269-273.*
Wikipedia, Indometacin, accessed Jul. 14, 2014, pp. 1-6.*
Gou, MaLing et al., J Biomed Mater Res 93A (2010), pp. 219-226.*
Zhang, Ji et al., Biomacromolecules, 7 (2006), pp. 2492-2500.*
Kim, Moon Suk, Wiley Periodicals, Inc, J Polym Sci Part A: Polym Chem, 44 (2006) pp. 5413-5423.*
Lee, Ju Young, et al, J. Mater. Chem, (2010, vol. 20, pp. 3265-3271 (pp. 1-18).*
Kim, Kyung Sook, et al., Tissue Engineering: Part A, vol. 15, No. 10 (2009) pp. 3201-3209.*
Chen, Huangqin, journal of bioactive and compatible polymers, vol. 23, Jan. 2008, pp. 38-48 (Year: 2008).*
Lee, Ju Young, et al., J. Mater. Chem., 2010, 20, pp. 3265-3271 (Year: 2010).*
Harish B. Ravivarapu et al., Polymer and microsphere blending to alter the release of a peptide from PLGA microspheres, European Journal of Pharmaceutics and Biopharmaceutics, 50(2000) 263-270, Jan. 31, 2000, pp. 263-270, Elsevier.
Byung Soo Kim et al; "BSA-FITC-loaded microcapsules for in vivo delivery"; Biomaterials 30 (2009) 902-909 pages; www.elsevier.com/locate/biomaterials.

* cited by examiner

*Primary Examiner* — Dennis J Parad
*Assistant Examiner* — Lyndsey Beckhardt
(74) *Attorney, Agent, or Firm* — Vorys, Sater, Seymour & Pease LLP; Mih Suhn Koh (57) ABSTRACT

Provided is a drug delivery system for control of initial burst of a drug. More particularly, there are provided a drug delivery formulation including: a granule containing a biodegradable polymer and a drug; and a temperature-sensitive hydrogel, and a method for preparing the same. The presently disclosed drug delivery formulation can be prepared via a relatively simple process and allows a drug to be released slowly at a constant rate without initial burst and thus maintains a constant blood level of the drug for a long period of time. Consequently, it is capable of preventing the initial burst of the existing injection-type drug delivery formulations and slow-release granules and providing a desired release profile, including sustained release with time.

3 Claims, 10 Drawing Sheets

DRUG DELIVERY FORMULATION FOR CONTROLLING OF INITIAL BURST AND MANUFACTURING METHOD THEREOF

CROSS-REFERENCE TO RELATED APPLICATIONS

This application claims priority under 35 U.S.C. § 119 to Korean Patent Application No. 10-2011-0003271, filed on Jan. 12, 2011, in the Korean Intellectual Property Office, the disclosure of which is incorporated herein by reference in its entirety.

BACKGROUND

(a) Technical Field

The present invention relates to a drug delivery system for control of initial burst of a drug. More particularly, the present invention relates to a drug delivery formulation including a granule containing a biodegradable polymer and a drug and a temperature-sensitive hydrogel, and a method for preparing the same.

(b) Background Art

Recently, with a growing interest in medical materials, research has been actively carried out on drug delivery formulations for delivering drugs for sustained time using functional materials. At present, granules are most actively studied and used in various fields, and research has been on the way to discover their new preparation methods, material developments, etc.

In the development of drug delivery systems, efforts are ongoing to maintain the minimum effective concentration of the drug in the bloodstream while minimizing side effects caused by its toxicity. However, in most cases, a blood level above a certain value induces tolerance, resulting in ever higher concentration of the drug to provide pharmacological effect at the targeted site. In this aspect, a constant drug release such as the zero-order release is not always effective for all cases, but development of new drug delivery methods such as externally- or self-controlled drug delivery systems, intelligent drug delivery systems, or the like is necessary.

Granule refers to a capsular material of micrometer-order size, consisting of a shell and a core material included therein. It usually has a diameter of 1-800 μm although the size is not particularly limited, and contains 10-90% of the core material based on weight. In general, the granule is designed such that the release rate of the functional core material can be controlled according to the chemical structure and thickness of the granular shell, which is made of thin synthetic or natural polymer film, and size of the granule. The core material may be a solvent, fragrance, drug, heat storage material, dye, ink, or the like. Depending on the component of the core material, the granules are widely used and studied in the field of medicine, agriculture (herbicides, insecticides, fungicides, germicides, etc.), food, cosmetics, and so forth. When the drug is prepared in granule for drug delivery, the drug becomes released without a uniform release profile or is released within a relatively short time. Therefore, research has been actively carried out recently so as to control the release rate of a drug and thereby to maximize its therapeutic effects. In particular, studies have been focused on the control of the initial burst of the drug from the surrounding material. And, with regard to the toxicity issue of the synthetic polymers used as a drug delivery carrier for control of the drug release, studies are also carried out about non-toxic carriers. In this regard, interests are increasing in the preparation of a granule for drug delivery using a biocompatible, biodegradable polymer.

Typical preparation methods of granules for drug delivery using polymers include phase separation, solvent extraction, solvent evaporation, spray drying, etc. Selection of a suitable preparation method is very crucial since the final properties of granule, such as particle size, drug release profile, drug entrapment, etc., are greatly affected by the preparation method.

In general, a slow-release granule formulation requires the drug release rate be suitably controlled and prevent the initial release rate from becoming excessively high. However, the granules prepared by the aforesaid conventional preparation methods cannot provide a constant drug release rate or release the drug initially in a burst. In many cases, if the initial release is reduced by adjusting the preparation parameters, the drug is not released initially or a consistent release is not achieved.

In an effort to solve these problems, two or more polymers having different rate of degradation were mixed to prepare a granule so as to control the rate drug release in the initial and subsequent stages [Ravivarapu, H. B., Burton, K., DeLuca, P. P., Polymer and microsphere blending to alter the release of a peptide from PLGA microspheres, *Eur. J. Pharm. Biopharm.*, 50(2), 263-70, 2000]. However, when two or more polymers are used to prepare a granule formulation, the degradation rate of the polymer which degrades faster affects that of the polymer which degrades slower, resulting in increased degradation rate of the granule as a whole. As a result, it is difficult to control the drug release in the initial and subsequent stages as desired.

To overcome the disadvantages of the granule formulation, U.S. Pat. No. 6,120,787 discloses a method of preparing core particles wherein a drug is entrapped and then coating the core particles with a biodegradable polymer by air-suspension coating. According to this method, the initial release rate is low because the core particles entrapping the drug are coated with a different biodegradable polymer. However, according to a test carried out by the inventors of the present invention, depending on the degree of coating, the drug is not released initially but is released only after a predetermined time. Further, since the air suspension technique requires a minimum production amount of tens of grams, it is limited in application to expensive drugs such as peptide or protein. In addition, it is not appropriate for actual commercial-scale production because the granule has to be prepared in two stages.

Accordingly, there is a need of development of a new formulation capable of preventing initial burst of a drug and controlling drug release consistently as desired, which can be prepared simply and economically.

SUMMARY

The inventors of the present invention have found out that, when a granule in which a drug is entrapped is mixed with a temperature-sensitive hydrogel, the temperature-sensitive hydrogel controls the drug to be released from the granule gradually in the initial stage, thus preventing initial burst of the drug into the bloodstream and providing controlled release of the drug at constant rate, thereby maintaining the blood level of the drug for a long period of time and maximizing its therapeutic effects.

The present invention is directed to providing a drug delivery formulation including a granule containing a biodegradable polymer and a drug and a temperature-sensitive hydrogel, and a method for preparing the same.

In one general aspect, the present invention provides a drug delivery formulation including: a granule containing a biodegradable polymer and a drug; and a temperature-sensitive hydrogel.

In another general aspect, the present invention provides a method for preparing a drug delivery formulation, including: (a) incorporating a drug into a biodegradable polymer having a molecular weight 10,000-200,000 g/mol to prepare a granule wherein the drug is entrapped; and (b) mixing the granule with a temperature-sensitive hydrogel to form a drug delivery formulation.

The above and other aspects and features of the present invention will be described infra.

BRIEF DESCRIPTION OF THE DRAWINGS

The above and other objects, features and advantages of the present invention will now be described in detail with reference to certain exemplary embodiments thereof illustrated in the accompanying drawings which are given hereinbelow by way of illustration only, and thus are not limitative of the disclosure, and wherein.

It should be understood that the appended drawings are not necessarily to scale, presenting a somewhat simplified representation of various preferred features illustrative of the basic principles of the disclosure. The specific design features of the disclosure as disclosed herein, including, for example, specific dimensions, orientations, locations and shapes, will be determined in part by the particular intended application and use environment.

DETAILED DESCRIPTION

Hereinafter, reference will now be made in detail to various embodiments of the present invention, examples of which are illustrated in the accompanying drawings and described below. While the disclosure will be described in conjunction with exemplary embodiments, it will be understood that the present description is not intended to limit the disclosure to those exemplary embodiments. On the contrary, the disclosure is intended to cover not only the exemplary embodiments, but also various alternatives, modifications, equivalents and other embodiments, which may be included within the spirit and scope of the disclosure as defined by the appended claims.

The present invention relates to a drug delivery system capable of controlling initial burst of a drug and providing gradual release. In order to overcome initial burst or rapid decrease or increase of drug release with time, a granule entrapping a drug is prepared first and then it is mixed with a temperature-sensitive hydrogel to prepare a drug delivery formulation whereby the release of the drug is controlled in two stages.

Accordingly, the present invention provides a drug delivery formulation including: a granule containing a biodegradable polymer and a drug; and a temperature-sensitive hydrogel. The present invention also provides a method for preparing a drug delivery formulation, including: (a) incorporating a drug into a biodegradable polymer having a molecular weight 10,000-200,000 g/mol to prepare a granule wherein the drug is entrapped; and (b) mixing the granule with a temperature-sensitive hydrogel to form a drug delivery formulation.

By controlling initial burst of the drug from the granule by the temperature-sensitive hydrogel after injection, the drug delivery formulation is capable of preventing initial burst of the drug into the bloodstream and controlling the release of the drug at constant rate, thereby maintaining the blood concentration of the drug constant for a long period of time.

Figure 1:
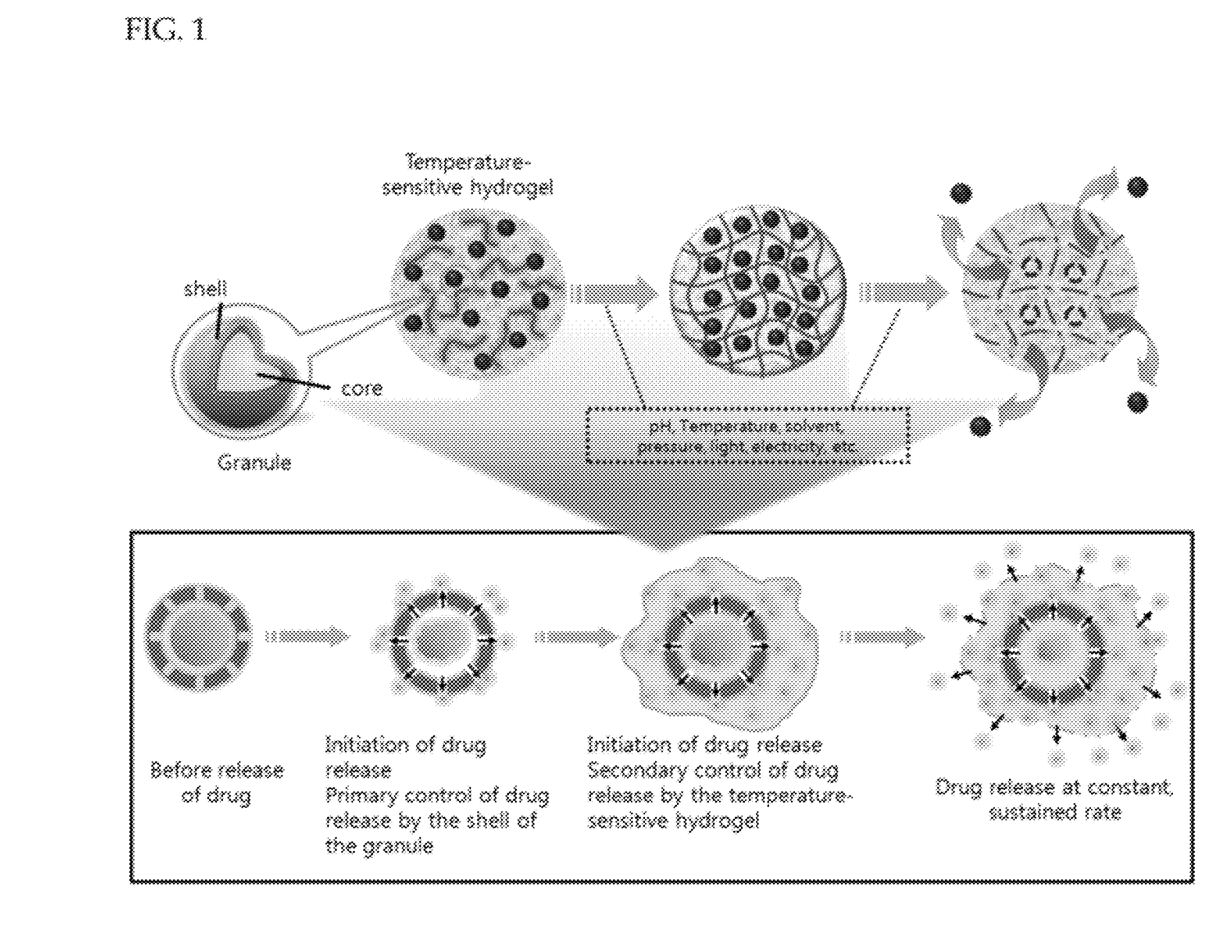
FIG. 1 schematically illustrates a granule and a temperature-sensitive hydrogel (top) and primary and secondary release control of a drug thereby (bottom), according to the present invention.

In the present invention, the biodegradable polymer is used as a shell enclosing the granule. The biodegradable polymer primarily controls the drug release rate depending on its kind and composition (FIG. 1). The biodegradable polymer entraps the drug as a core material and thus forms the granule. In the present invention, the biodegradable polymer, which is biocompatible and biodegradable, serves as the shell of the granule and primarily controls the amount and rate of drug release depending on the kind and composition thereof.

Examples of the biodegradable polymer include synthetic polymers such as polycaprolactone, polyalkylcarbonate, polyamino acid, polyhydroxybutyric acid, polyorthoester, polyanhydride, Pluronic (poly(ethylene oxide)-poly(propylene oxide)-poly(ethylene oxide)), polylactide (PLA), polyglycolide (PGA), poly(lactide-co-glycolide) (PLGA), poly(lactide-co-glycolide)-glucose (PLGA-glucose), etc., and natural polymers such as carboxymethyl cellulose, algin, alginic acid or alginate, hyaluronic acid, polypeptide or protein, gelatin or casein, chitin derivatives and chitosan, etc.

Specifically, the biodegradable polymer may be PLGA, a copolymer of lactide and glycolide. The biodegradable polymer is capable of controlling the amount and rate of drug release depending on its kind and composition. For example, the degradation rate of PLGA in vivo is determined by the compositional proportion of PLA and PGA, and thus the drug release rate can be controlled therethrough. Therefore, the drug release rate can be controlled when such a biodegradable polymer is used as a matrix for drug release control.

The PLGA copolymer as the biodegradable polymer may have a molecular weight of 20,000-200,000 g/mol, specifically 30,000-90,000 g/mol. The release rate becomes different depending on the molecular weight of the polymer. A polymer having a small molecular weight leads to fast release, whereas one with a large molecular weight leads to slow release. Accordingly, a polymer having a suitable molecular weight may be selected to attain a desired controlled release of the granule.

Among the above-described biodegradable polymers, PLGA is approved by the US Food and Drug Administration as a non-toxic biodegradable polymer that can be used for use in human body and has long been used widely for tissue regeneration materials, drug delivery carriers or surgical sutures, with proven biocompatibility.

Specifically, the drug that can be used in the present invention may include an anti-arthritic drug, a hormone, a bone metabolism agent, an immunosuppressant, an anti-angiogenic agent, a vitamin, a protein or peptide drug, an anti-cancer agent, an analgesic, an anti-inflammatory agent, an anti-ulcer agent and an anti-diabetic drug, but is not limited thereto. Specifically, it may be a protein drug which provides limited effect when orally administered.

The drug may be incorporated into the biodegradable polymer to prepare the granule in which the drug is entrapped. The granule may further comprise one or more additive such as an antiseptic, a preservative, a vehicle, or the like. The incorporation may be performed by ultrasonic spraying [B. S. Kim, J. M. Oh, K. S. Kim et al., *Biomaterials*, 30, 902 (2009); B. S. Kim, J. M. Oh, H. Hyun et al., *Molecular Pharmaceutics*, 6, 353 (2009)] or using a syringe. Through the ultrasonic spraying, a granule with different compositions at the core portion and the outer coating portion may be prepared. In this case, a superior drug entrapment ratio of about 60-70% can be achieved and the initial burst of the drug is reduced. However, since the drug is still released in large amounts in the initial stage with this measure only, the prepared granule is mixed with the temperature-sensitive hydrogel in order to solve the initial release problem and provide consistently controlled drug release.

The temperature-sensitive hydrogel is a polymer exhibiting abrupt change in solubility depending on temperature change. It exists as sol at room temperature but forms gel around the human body temperature. As such, it can be utilized to effectively control the drug release, as an intelligent hydrogel that can be used without surgical operation. The temperature-sensitive hydrogel may be prepared from synthetic or natural polymers such as Pluronic, polycaprolactone, methoxypolyethylene glycol-polycaprolactone (MPEG-PCL), carboxymethyl cellulose (CMC), algin, alginic acid or alginate, polypeptide or protein, gelatin or casein, chitin derivatives and chitosan. The hydrogel may be prepared by adding these polymers to, for example, a phosphate buffer solution. However, the preparation method is not limited thereto but various methods may be employed depending on the kind of the polymer.

The drug delivery formulation according to the present invention may be used for injection, but without being limited thereto.

EXAMPLES

The examples and experiments will now be described. The following examples and experiments are for illustrative purposes only and not intended to limit the scope of this disclosure.

Preparation Example 1: Synthesis of Methoxypolyethylene glycol-polycaprolactone (MPEG-PCL) Block Copolymer To synthesize an MPEG-PCL block copolymer having a molecular weight of 3,150 g/mol, MPEG (1.5 g, 2 mmol, $M_n$=750 g/mol) and toluene (80 mL) were added to a well-dried, 100 mL round-bottom flask equipped with a Dean-Stark trap, and azeotropic distillation was carried out for 3 hours at 130° C. Upon completion of the distillation, toluene was completely removed and MPEG was cooled to room temperature. Then, purified caprolactone (CL, 4.8 g, 42 mmol) was added using a syringe. After adding purified methylene chloride (MC, 40 mL) as a reaction solvent, HCl/Et$_2$O (4 mL) was added as a polymerization catalyst, and the reaction mixture was stirred for 24 hours at room temperature. All the procedures were carried out under high-purity nitrogen atmosphere. Upon completion of the reaction, the product was precipitated by slowly dropping on hexane (1,000 mL) in order to remove unreacted monomers or initiator. The precipitate was dissolved in MC and filtered through filter paper. After removing the solvent using a rotary evaporator, the product was dried under reduced pressure.

The molar composition and molecular weight of the synthesized copolymer was analyzed by $^1$H-NMR. The molecular weight was similar to the theoretically expected value. Gel permeation chromatography (GPC) revealed a polydispersity of 1.26.

Preparation Example 2: Synthesis of MPEG-PCL-co-polylactide (MPEG-PCL-co-PLA) Block Copolymer (CL:Lactide=90:10)

To synthesize an MPEG-PCL-co-PLA block copolymer having a molecular weight of 50,750 g/mol, MPEG (0.05 g, 6.7×10$^{-2}$ mmol) and toluene (80 mL) were added to a well-dried, 100 mL round-bottom flask equipped with a Dean-Stark trap, and azeotropic distillation was carried out for 3 hours at 130° C. Upon completion of the distillation, toluene was removed and MPEG was cooled to 25° C. Then, after adding purified CL (3 g, 26.3 mmol) and lactide (LA, 0.42 g, 2.92 mmol) and purified toluene (40 mL), as a reaction solvent, Sn(Oct)$_2$ (0.1 mL) was added as a polymerization catalyst, and the reaction mixture was stirred for 24 hours at 120° C. All the procedures were carried out under high-purity nitrogen atmosphere. Upon completion of the reaction, the product was precipitated by slowly dropping on a mixture of hexane (900 mL) and ether (100 mL) in order to remove unreacted monomers or initiator. The precipitate was dissolved in MC and filtered through filter paper. After removing the solvent using a rotary evaporator, the product was dried under reduced pressure.

The molar composition and molecular weight of the synthesized copolymer was analyzed by $^1$H-NMR. The molecular weight was similar to the theoretically expected value as 50,300 g/mol.

Preparation Example 3: Preparation of Granule by Ultrasonic Spraying

Figure 2:
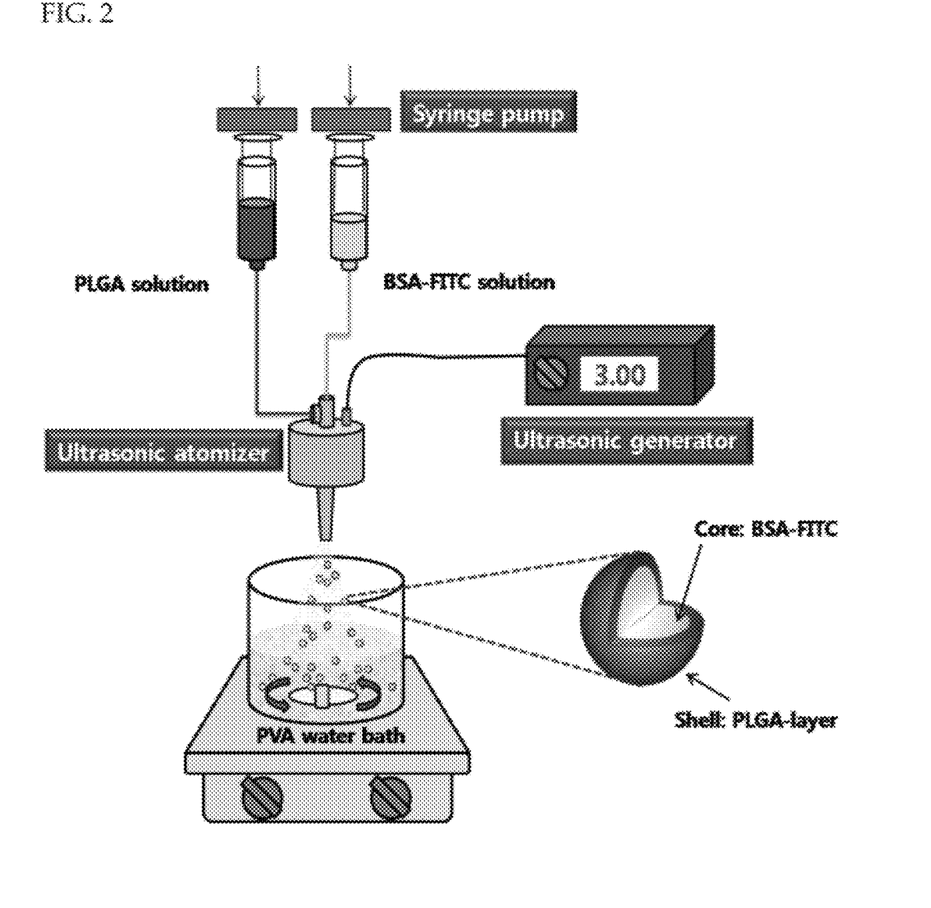
FIG. 2 schematically illustrates a method for preparing a polymer granule according to the present invention.
Figure 3:
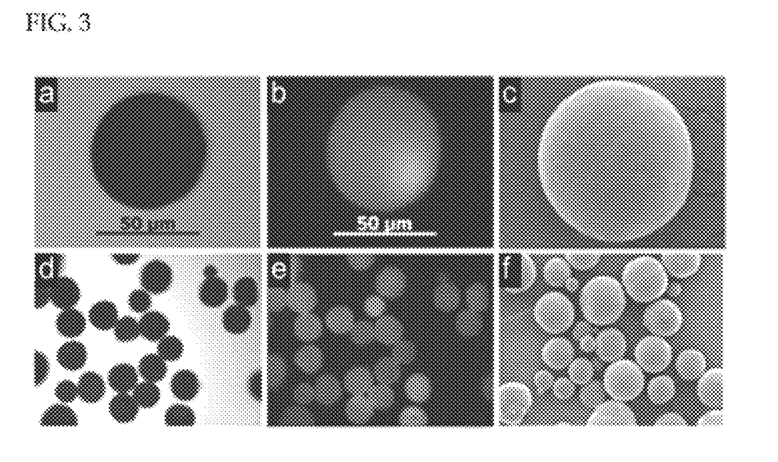
FIG. 3 shows fluorescence microscopic and scanning electron microscopic (SEM) images of the granule prepared in Preparation Example 1.

Poly(lactide-co-glycolide) (PLGA) having a molecular weight of 33,000 g/mol was dissolved in ethyl acetate to 3 wt %. As a model drug, the water-soluble protein bovine serum albumin (BSA) to which the fluorophore FITC is attached (BSA-FITC) was dissolved in distilled water to 5 wt % to prepare a uniform drug suspension. Each solution was put in a syringe and ultrasonically sprayed at a flow rate of 4 and 0.2 mL/min, respectively. After preparing a 0.5 wt % aqueous solution of polyvinyl alcohol (PVA), the polymer solution and the drug suspension were sprayed at an oscillation frequency of 60 Hz to disperse them in the PVA solution, so as to form granules. Then, after stabilizing by stirring at 700 rpm for 2 hours at room temperature, the resulting granules were separated, washed with distilled water, and freeze dried to obtain polymer granules entrapping the protein drug (FIG. 2).

Preparation Example 4: Preparation of Granule Using Syringe

Figure 4:
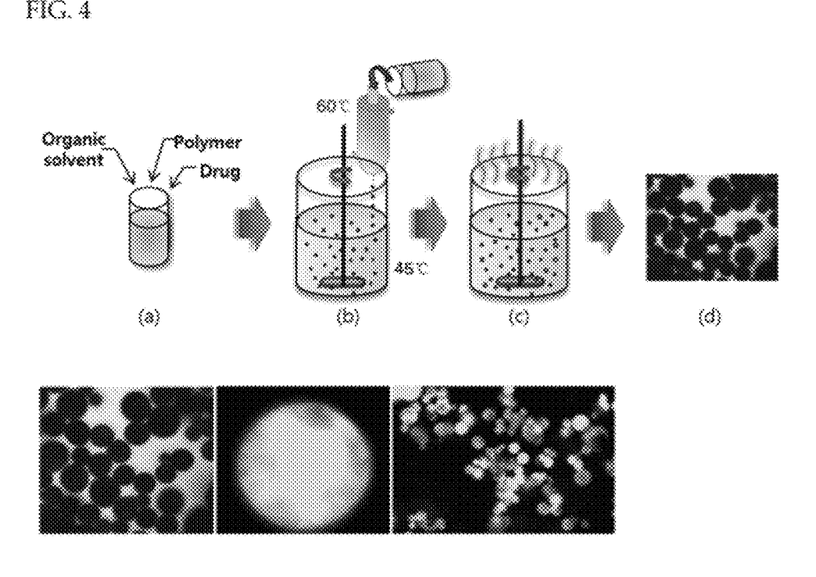
FIG. 4 schematically illustrates a method for preparing a polymer granule in Preparation Example 2 and shows fluorescence microscopic images of the granule entrapping a drug.
Figure 5:
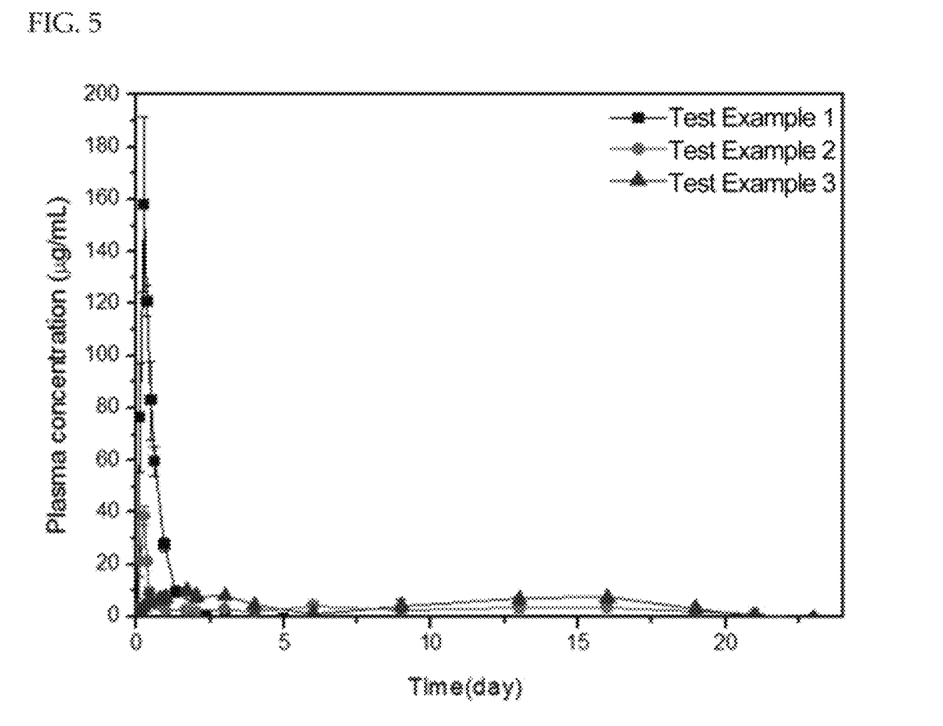
FIG. 5 shows a result of Test Examples 1-3 as blood concentration of a drug with time.

The MPEG-PCL-co-PLA block copolymer (0.2 g) prepared in Preparation Example 2 and BSA-FITC (20 mg) were stirred in THF (0.7 mL) and then incubated at 60° C. for 30 minutes to prepare a drug suspension in which BSA-FITC is dispersed in the copolymer. After preparing a 1 wt % aqueous solution of PVA at 45° C., the BSA-FITC suspension was sprayed dispersed in the PVA solution using a syringe, as illustrated in FIG. 4, so as to form granules. Then, evaporation of the solvent and formation of granules were induced by slowly cooling to room temperature while stirring for 2 hours. The resulting granules were separated, washed with distilled water, and freeze dried to obtain polymer granules entrapping the BSA-FITC.

Preparation Example 5: Preparation of Pluronic Hydrogel

Pluronic ($M_n$=12,000 Da) was added to a phosphate buffer solution (PBS, pH 7.4) to 20 wt % and stirred at 4° C. The resulting solution was stored in a refrigerator at 4° C. for 2 days.

Preparation Example 6: Preparation of Carboxymethyl Cellulose (CMC) Hydrogel

Low-viscosity CMC (viscosity=50-200 cP, Batch No. 078K0164) was added to PBS (pH 7.4) to 3 wt %, completely dissolved by stirring at room temperature for 1 day, and stored in a refrigerator at 4° C. for 2 days.

Preparation Example 7: Preparation of CMC/polyethyleneimine (PEI) Hydrogel

A CMC solution was prepared by dissolving low-viscosity CMC (viscosity=50-200 cP) in PBS (pH 7.4) to 3 wt %. A 44 wt % PEI solution was prepared using PEI having a molecular weight of 423 g/mol and hydrochloric acid (HCl) at molar ratio of 1:1. The CMC solution and the PEI solution were mixed at a weight ratio of 90:10 to prepare CMC/PEI hydrogel.

Preparation Example 8: Preparation of Chitosan Hydrogel

A 0.1 mol/L chitosan solution was prepared by dissolving medium molecular weight chitosan (viscosity=200-800 cP, Batch No. 03318AJ) in acetic acid (18 mL), adding the solution (4 mL) to a 5 mL vial, followed by stirring. Then, β-glycerophosphate disodium salt hydrate dissolved in distilled water (1 mL) was slowly added to the chitosan solution, at 20 wt % based on the chitosan solution, using a syringe. The resulting solution was stabilized by stirring slowly at 4° C. for 1.5 hours to prepare chitosan hydrogel.

Preparation Example 9: Preparation of MPEG-PCL Hydrogel

The MPEG-PCL block copolymer prepared in Preparation Example 1 was completely dissolved in PBS (pH 7.4) at 20 wt %. Then, the resulting solution was stored in a refrigerator at 4° C. for 2 days.

Example 1: In Vivo Injection of Injection Formulation Prepared by Uniformly Dispersing Granule (Preparation Example 3) in Pluronic Hydrogel (Preparation Example 5)

The granules entrapping the drug (2 mg) prepared in Preparation Example 3 were uniformly dispersed in the Pluronic hydrogel (1 mL) prepared in Preparation Example 5 and added to a 1 mL syringe to prepare an injection formulation. Immediately, the prepared injection formulation was subcutaneously injected to a mouse to form gels.

Example 2: In Vivo Injection of Injection Formulation Prepared by Uniformly Dispersing Granule (Preparation Example 3) in CMC Hydrogel (Preparation Example 6)

An injection formulation was prepared and subcutaneously injected in the same manner as Example 1, except for using the CMC hydrogel prepared in Preparation Example 6.

Example 3: In Vivo Injection of Injection Formulation Prepared by Uniformly Dispersing Granule (Preparation Example 3) in CMC/PEI Hydrogel (Preparation Example 7)

An injection formulation was prepared and subcutaneously injected in the same manner as Example 1, except for using the CMC/PEI hydrogel prepared in Preparation Example 7.

Example 4: In Vivo Injection of Injection Formulation Prepared by Uniformly Dispersing Granule (Preparation Example 3) in Chitosan Hydrogel (Preparation Example 8)

An injection formulation was prepared and subcutaneously injected in the same manner as Example 1, except for using the chitosan hydrogel prepared in Preparation Example 8.

Example 5: In Vivo Injection of Injection Formulation Prepared by Uniformly Dispersing Granule (Preparation Example 3) in MPEG-PCL Hydrogel (Preparation Example 9)

An injection formulation was prepared and subcutaneously injected in the same manner as Example 1, except for using the MPEG-PCL hydrogel prepared in Preparation Example 9.

Comparative Example 1: Preparation of BSA-FITC Solution

BSA-FITC (2 mg) was completely dissolved in PBS (pH 7.4, 1 mL) to prepare an injection formulation.

Comparative Example 2: Preparation of Granule-Only Solution 1.99 mg of granules obtained in Preparation Example 3, 20% (w/v) solution of D-mannitol (5 wt %), CMC (2 wt %) and 0.1% Tween 80 were uniformly dispersed in distilled water and added to a 1 mL syringe to prepare an injection formulation.

Test Example 1: Injection of BSA-FITC Solution Followed by Taking of Serum from Tail Vein The BSA-FITC drug solution (1 mL) prepared in Comparative Example 1 was subcutaneously injected to a mouse using a syringe. Blood was taken from the tail vein of the mouse at different times, which was added to an Eppendorf tube containing 200 μL of a mixture solution of heparin:distilled water (1:499) and then centrifuged. Upon centrifugation, red blood cells sink and serum is obtained as the supernatant. The supernatant (200 μL) was taken and, after adding distilled water (100 μL), 66 mM ethylenediaminetetraacetic acid (EDTA, 300 μL) and 50 mM N-2-hydroxyethylpiperazine-N'-2-ethanesulfonic acid (HEPES, 400 μL), the amount of BSA-FITC remaining in the blood was measured using a fluorescence spectrometer.

The blood was taken at 30 minutes, 1 hour, 2 hours, 3 hours, 6 hours, 9 hours, 12 hours and 24 hours after the injection of the formulation and at the same hours from the following days. In order to measure drug release, fluorescence intensity from the sample was measured quantitatively using a fluorescence spectrometer (Jasco, FP-6500) in the dark, with an excitation wavelength of 490 nm and an emission wavelength of 525 nm.

Figure 6:
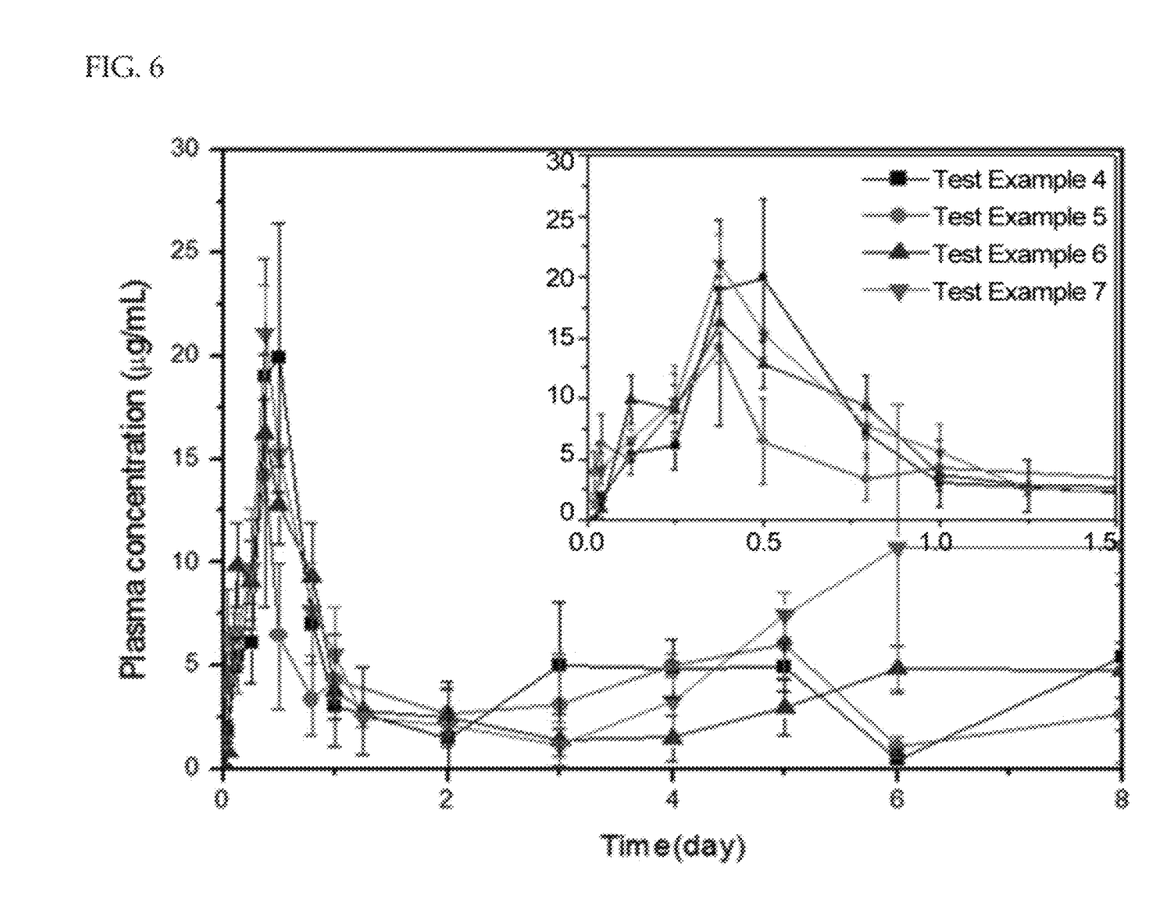
FIG. 6 shows a result of Test Examples 4-7 as blood concentration of a drug with time.

Comparative Example 1 showed excessive drug release. All drugs were released in short time. In contrast, Test Example 2 exhibited initial drug release reduced by about 25% as compared to Comparative Example 1. Test Example 3, wherein a gradual drug release formulation was used, exhibited consistent drug release without initial burst (FIG. 6).

Test Example 2: Injection of Granule-Only Solution Followed by Taking of Serum from Tail Vein Drug release was measured in the same manner as Test Example 1, except for using the granule-only solution prepared in Comparative Example 2.

Test Example 3: Injection of Pluronic Hydrogel Followed by Taking of Serum from Tail Vein Drug release was measured in the same manner as Test Example 1, except for using Pluronic hydrogel.

Test Example 4: Injection of CMC Hydrogel Followed by Taking of Serum from Tail Vein Drug release was measured in the same manner as Test Example 1, except for using CMC hydrogel.

Test Example 5: Injection of CMC/PEI Hydrogel Followed by Taking of Serum from Tail Vein Drug release was measured in the same manner as Test Example 1, except for using CMC/PEI hydrogel.

Test Example 6: Injection of Chitosan Hydrogel Followed by Taking of Serum from Tail Vein Drug release was measured in the same manner as Test Example 1, except for using chitosan hydrogel.

Test Example 7: Injection of MPEG-PCL Hydrogel Followed by Taking of Serum from Tail Vein Drug release was measured in the same manner as Test Example 1, except for using MPEG-PCL hydrogel.

Test Example 8: Gel Formation of Gradual Drug Release Formulation In Vivo

Figure 7:
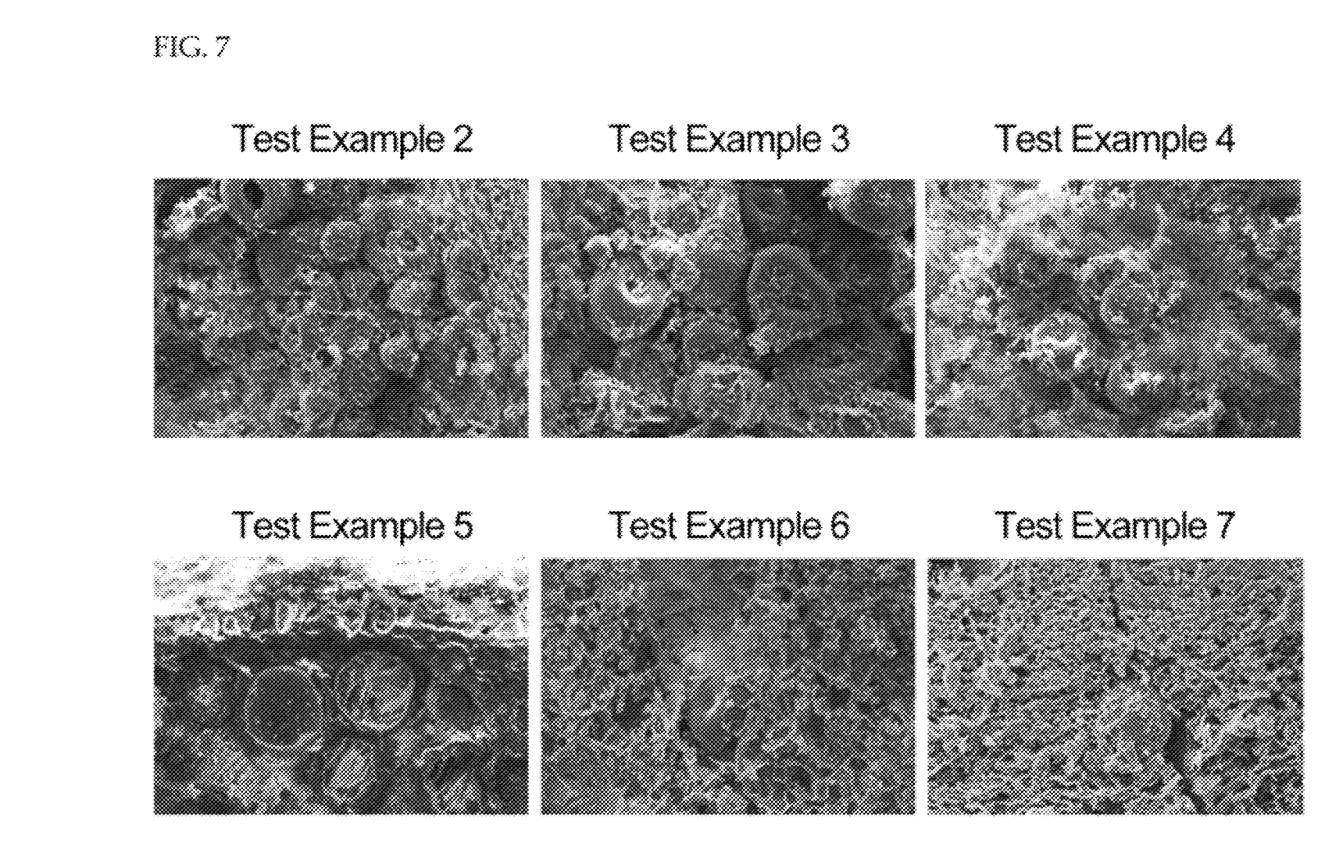
FIG. 7 shows SEM images of gels obtained one day after the subcutaneous injection of an aqueous solution of the hydrogel in Comparative Example 2 and Examples 1-5 to a mouse.
Figure 8:
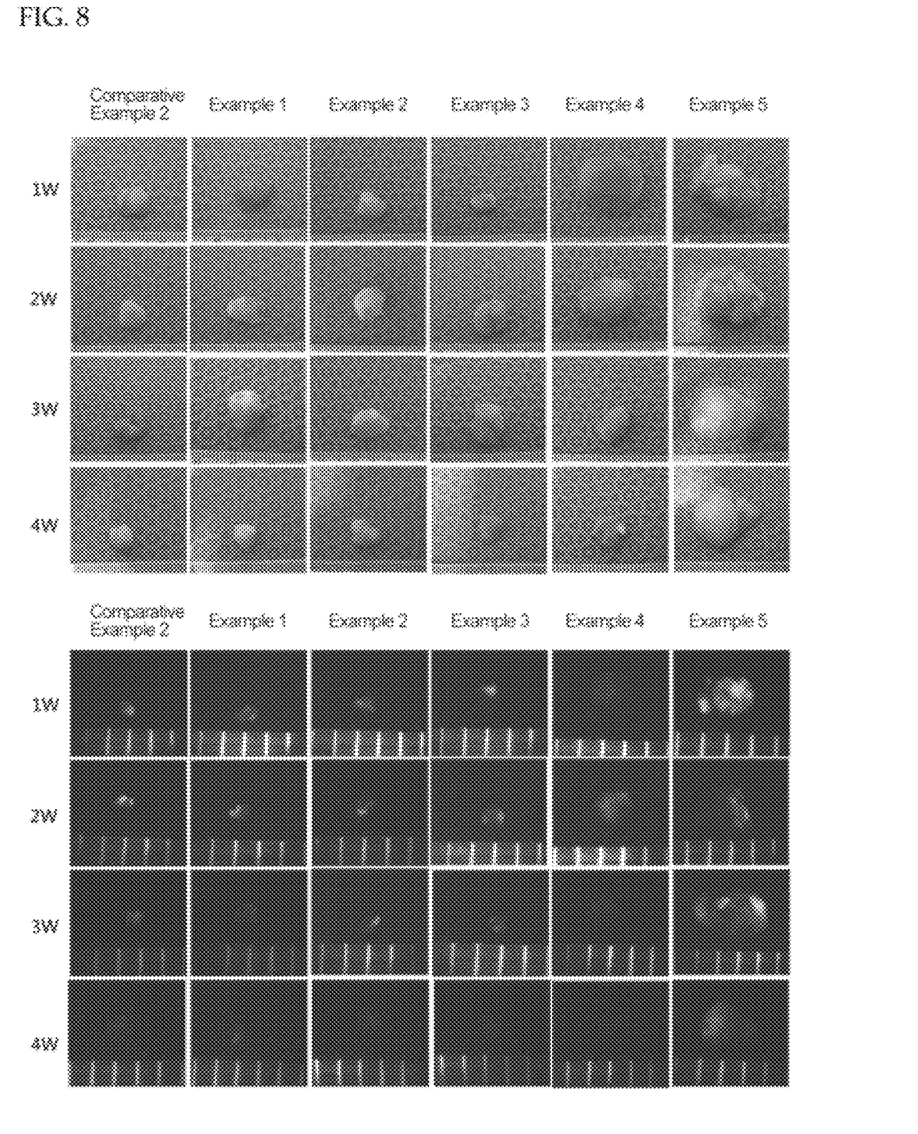
FIG. 8 compares the size of the gels obtained by subcutaneous injection of the aqueous solution of the hydrogel in Comparative Example 2 and Examples 1-5 to a mouse with time and shows fluorescence images photographed using a fluorescence spectrometer.

Gradual drug release formulations were kept in sol state at room temperature and subcutaneously injected (1 mL each) to a mouse using a disposable syringe. One day later, the injection site was cut open to confirm the formation of gels. The morphology was observed by scanning electron microscopy (SEM) (FIG. 7). As seen from the figure, the formulations of Examples 1-5 and Comparative Example 2 showed a lot of the granules distributed in the tissue. Except for Examples 4 and 5, all the formulations showed decrease in size at weeks 1, 2, 3 and 4, as the granules were biodegraded. The formulations of Examples 4 and 5 showed little change in size even after 4 weeks. This trend was also observed in the fluorescence images. The measurement of fluorescence intensity at weeks 1, 2, 3 and 4 revealed that the smaller the size of the granules, i.e., the more drug was released as the formulation was biodegraded with time, the smaller was the amount of the drug remaining in the formulation. In contrast, in Examples 4 and 5, more drug was remained in the formulation even after 4 weeks as compared to other formulations (FIG. 8).

Figure 9:
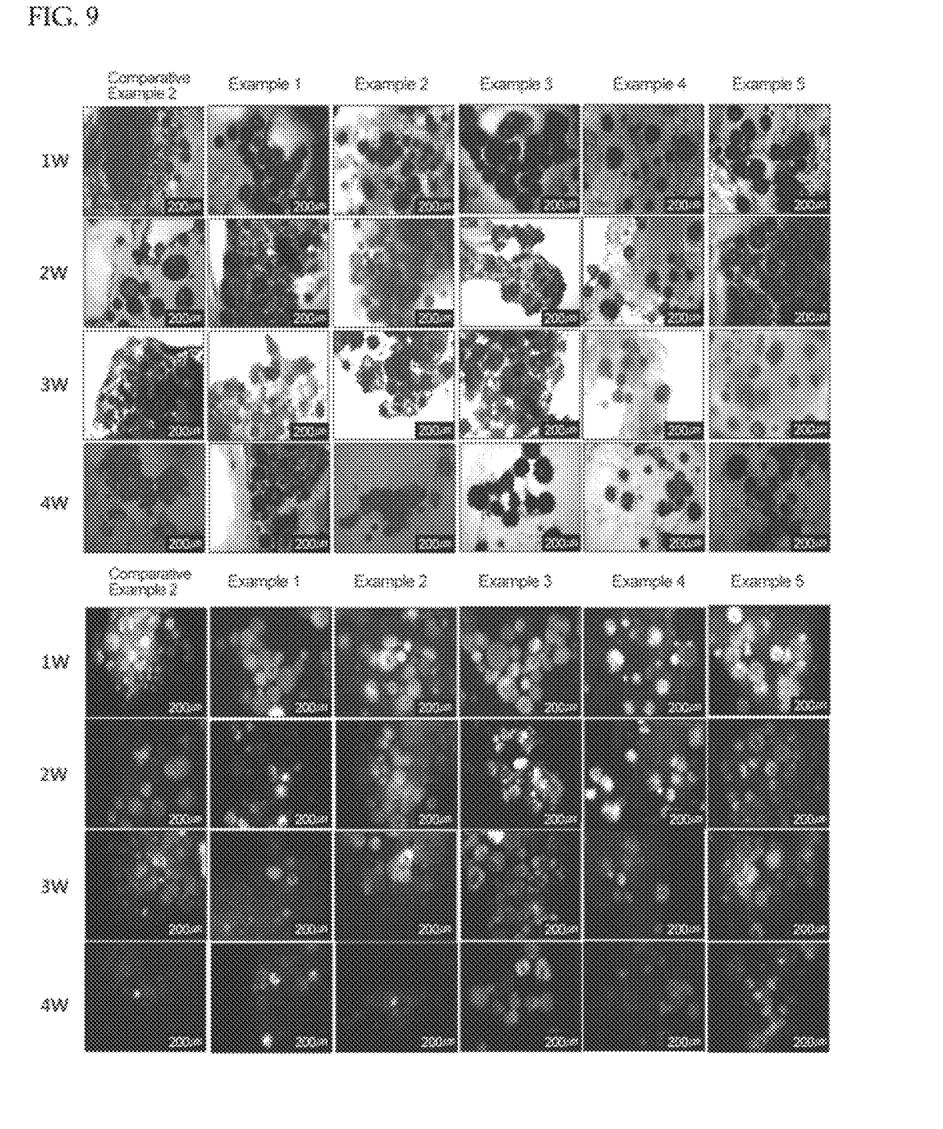
FIG. 9 shows microscopic images of the gels obtained after subcutaneous injection of the aqueous solution of the hydrogel in Comparative Example 2 and Examples 1-5 to a mouse.

The formulations taken from the subcutaneous tissue were frozen rapidly using liquid nitrogen and, after cutting, the cut cross-section was observed under a fluorescence microscope. A similar difference in the amount of drug in the formulation was observed with time (FIG. 9).

Thus, it was confirmed that the gradual drug release formulations according to the present invention can control rate and period of drug release depending on the composition of the two or more biodegradable polymers entrapping the drug.

Figure 10:
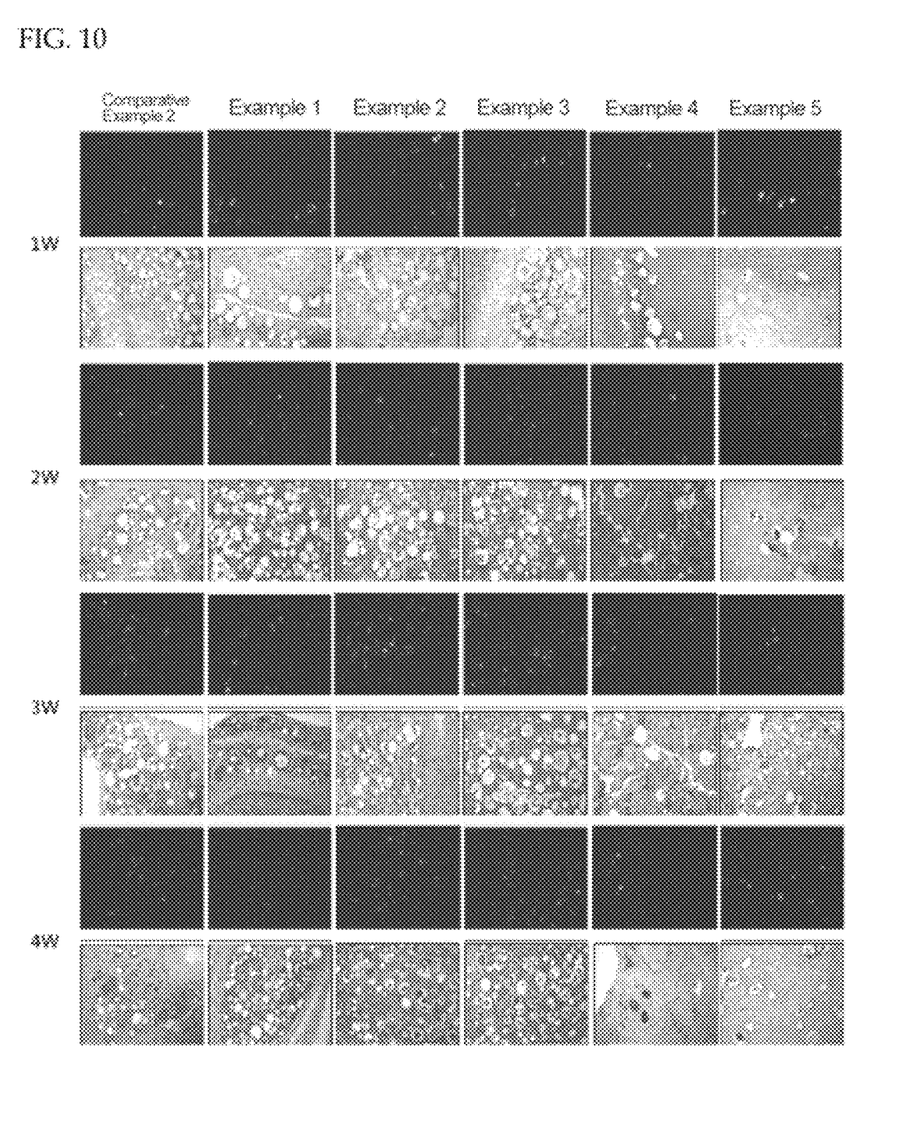
FIG. 10 shows hematoxylin and eosin (H&E) staining images of the gels obtained after subcutaneous injection of the aqueous solution of the hydrogel in Comparative Example 2 and Examples 1-5 to a mouse.
Figure 11:
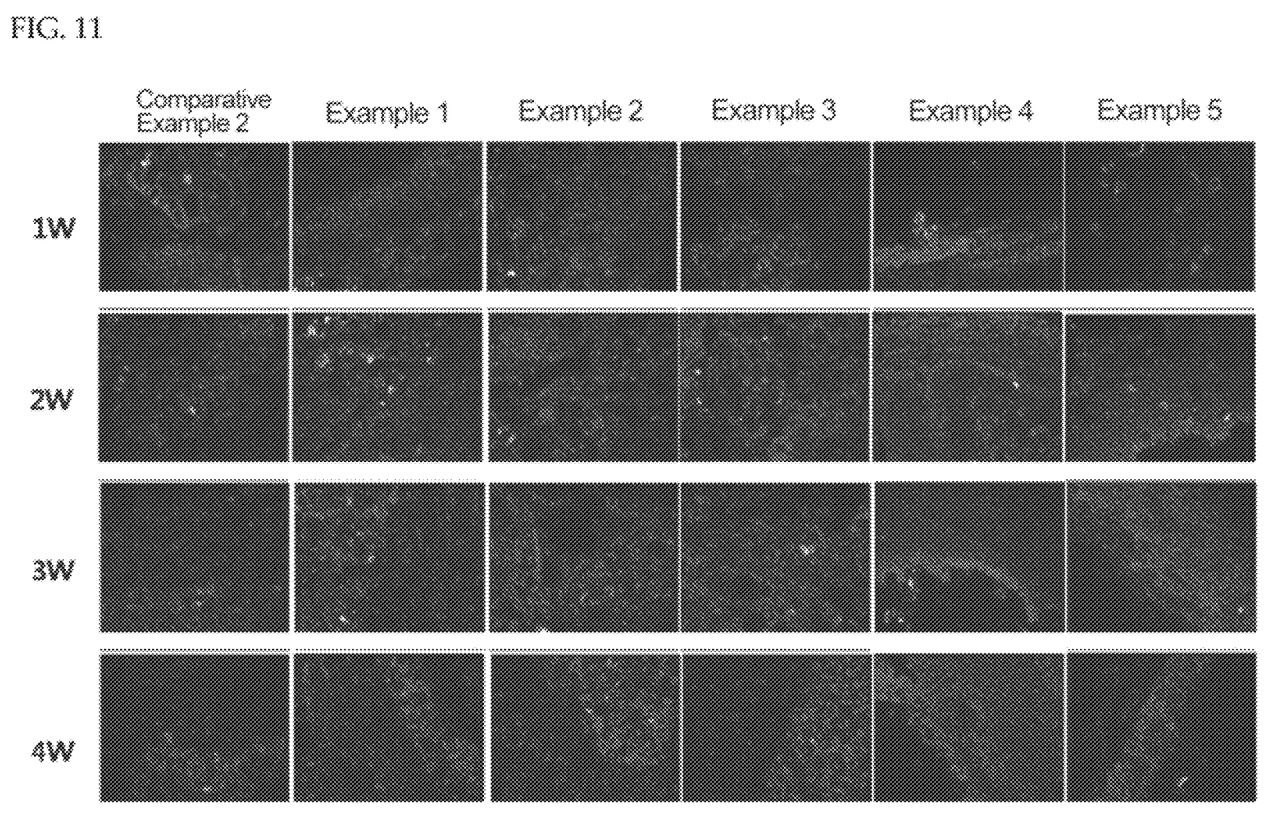
FIG. 11 shows ED1 immunostaining images of the gels obtained after subcutaneous injection of the aqueous solution of the hydrogel in Comparative Example 2 and Examples 1-5 to a mouse (The red and blue areas are the sites stained by DAPI and ED1, respectively, and the green area is where FITC emits fluorescence.

Test Example 9: Immunohistological Observation of Gradual Drug Release Formulations The formulations taken removed the subcutaneous tissue were fixed with 10% formalin at weeks 1, 2, 3 and 4. The fixed formulations were prepared into paraffin blocks, which were sliced into 4 μm thickness, fixed on a slide, and stained with hematoxylin and eosin (H&E) and ED1 for histological observation. H&E staining is the most basic staining method, which involves staining with nucleus-specific hematoxylin and cytoplasm-specific eosin. It allows the observation of overall cell behavior and morphology of cells. The H&E staining revealed the presence of macrophages, neutrophils and lymphocytes in the formulations and the distribution of the granules in the formulations could be observed (FIG. 10). Further, the expression of ED1 (mouse anti rat CD68; Serotec, UK) was investigated in order to confirm inflammatory response of the formulations (FIG. 11).

The experiment confirmed that the granules of the present invention are biocompatible, without inducing inflammatory immune responses, and thus can be used as a support for tissue engineering.

The drug delivery formulation according to the present invention, which is prepared by entrapping a drug in a granule made of a biodegradable polymer, for example, by ultrasonic spraying to prepare a slow-release granule, and then mixing it with a temperature-sensitive hydrogel prepared from a biodegradable, biocompatible synthetic polymer, is advantageous in that it can be prepared via a relatively simple process. Further, the gradual drug release formulation is advantageous in that the drug is releases at a constant rate without initial burst, thus providing a constant blood concentration of the drug for a long period of time. Hence, it is capable of preventing the initial burst problem of the conventional injection-type drug delivery formulations and slow-release granules and providing a desired release profile, including sustained release with time.

The present invention has been described in detail with reference to specific embodiments thereof. However, it will be appreciated by those skilled in the art that various changes and modifications may be made in these embodiments without departing from the principles and spirit of the disclosure, the scope of which is defined in the appended claims and their equivalents.

What is claimed is:

1. A drug delivery formulation comprising a plurality of granules suspended in a temperature-sensitive hydrogel, each granule comprising a biodegradable polymer forming the shell of the granule and a protein or peptide drug forming the core of the granule
    wherein the temperature-sensitive hydrogel is carboxymethyl cellulose(CMC)/polyethyleneimine(PEI) hydrogel,
    wherein the biodegradable polymer is poly(lactide-co-glycolide)(PLGA), and
    wherein the drug release is controlled by the shell of the granule and then by the temperature-sensitive hydrogel, reducing the initial burst of the drug and obtaining a sustained release of the drug.

2. A method for preparing the drug delivery formulation according to claim 1, comprising:
    incorporating a protein or peptide drug into a biodegradable polymer having a molecular weight 10,000-200,000 g/mol to prepare a granule wherein the drug is entrapped; and
    mixing a plurality of the prepared granules with a temperature-sensitive hydrogel to suspend the plurality of granules in the temperature-sensitive hydrogel to form a drug delivery formulation,
    wherein the biodegradable polymer is PLGA, and the temperature-sensitive hydrogel is carboxymethyl cellulose(CMC)/polyethyleneimine(PEI) hydrogel.

3. The method for preparing the drug delivery formulation according to claim 1, wherein the incorporation is performed by ultrasonic spraying or using a syringe.

* * * * *